United States Patent [19]
Jho et al.

[11] Patent Number: 6,013,028
[45] Date of Patent: Jan. 11, 2000

[54] TISSUE SPREADING INSTRUMENT FOR USE IN NARROW PASSAGE

[75] Inventors: Hae-Dong Jho, Pittsburgh, Pa.; John A. Redmond, Mundelein, Ill.

[73] Assignee: Integra NeuroCare LLC, Plainsboro, N.J.

[21] Appl. No.: 09/298,783

[22] Filed: Apr. 23, 1999

[51] Int. Cl.$^7$ .................................................. A61B 17/02
[52] U.S. Cl. .................. 600/204; 600/219; 600/235; 606/190
[58] Field of Search ................................ 600/201, 204, 600/210, 214, 217, 219, 235; 606/190, 199

[56] References Cited

U.S. PATENT DOCUMENTS

| | | | |
|---|---|---|---|
| 3,664,330 | 5/1972 | Deutsch | 600/235 X |
| 3,750,652 | 8/1973 | Sherwin | 128/17 |
| 4,385,628 | 5/1983 | Straith | 606/199 X |
| 4,574,804 | 3/1986 | Kurwa | 606/190 |
| 5,201,752 | 4/1993 | Brown et al. | 606/190 |
| 5,293,863 | 3/1994 | Zhu et al. | 600/214 |
| 5,429,121 | 7/1995 | Gadelius | 600/217 |
| 5,522,839 | 6/1996 | Pilling | 600/204 X |
| 5,782,859 | 7/1998 | Nicholas et al. | 600/204 X |

OTHER PUBLICATIONS

Jho et al, "Endoscopic Pituitary Surgery", Neurosurgical Operative Atlas, vol. 5, No. 1, pp. 1–12 (1996).
Jho et al, "Endoscopic endonasal transsphenoidal surgery: experience with 50 patients", Neurosurg Focus 1(1): Article 2 (1996).
Jho et al, "Endoscopic Pituitary Surgery: An Early Experience" Surg Neurol, 47:213–23 (1997).
Jho et al, "Endoscopic Endonasal Pituitary Surgery: Technical Aspects", vol. 19, No. 6 (Mar. 1997).

*Primary Examiner*—Jeffrey A. Smith
*Attorney, Agent, or Firm*—Skarsten Law Offices S.C.

[57] ABSTRACT

An instrument is provided for use by a surgeon to separate the nasal septum from the sphenoid sinus wall of a patient, in a procedure which may be performed very rapidly and with significantly reduced trauma to the septum. The instrument may be very usefully employed in connection with endoscopic endonasal pituitary surgery, although it is not limited thereto. The instrument comprises an elongated support member having first and second ends in opposing relationship, and further comprises pivotable and fixed jaw members respectively joined to the first end of the support member. Each of the jaw members has a length dimension measured from the support member, wherein the length of the pivotable jaw member exceeds the length of the fixed jaw member by a specified amount. A handle component joined to the second end of the support member is movable between first and second handle positions, to move the pivotable member in corresponding relationship between closed and open positions. Teeth mounted on the pivotable jaw member engage the septum to enhance detachment of the septum from the sphenoid sinus wall.

17 Claims, 6 Drawing Sheets

TISSUE SPREADING INSTRUMENT FOR USE IN NARROW PASSAGE

BACKGROUND OF THE INVENTION

The invention disclosed and claimed herein generally pertains to a surgical instrument of a type which may be inserted into and operated within a body cavity or passage of a patient, wherein the cavity or passage is very narrow and spatially confining. More particularly, the invention pertains to an instrument of such type which is especially well suited for use in breaking apart the nasal septum from its attachment to the sphenoidal sinus wall in order to provide an opening therethrough. Even more particularly, the invention pertains to an instrument of such type which is intended to reduce trauma resulting from the tearing of tissue and expedite access to the pituitary gland.

As is well known by those of skill in the art, an innovative procedure has recently been developed for removing tumors from the pituitary gland of a patient. In accordance therewith, a microsurgical instrument and an endoscope are inserted through the patient's nostril, to reach the anterior wall of the sella which is located at the rear of the nasal cavity. A section of the sella, which is a thin layer of bone, is removed by means of endoscopic surgery to expose the tumor. Further endoscopic tasks are then performed, to remove the tumor. This procedure, whereby the tumor is accessed through a patient's nasal cavity, has proven to be much less traumatic than prior art techniques, and is described for example, in an article entitled "Endoscopic Endonasal Pituitary Surgery: Technical Aspects" by Dr. Hae-Dong Jho, one of the inventors herein, Contemporary Neurosurgery, Vol.19. No.6 (March 1997). The procedure is further described in "Endoscopic Pituitary Surgery", Jho et al, Neurosurgical Operative Atlas, Vol. 6 No.1(1996).

In the above procedure, a passage must be formed through the patient's nasal cavity as a necessary preliminary step. The nasal septum comprises a sheath-like barrier formed of cartilaginous and bony tissue, and is attached to the middle of the sphenoid sinus wall. Its attachment has to be broken, in order to access the sella and the tumor. The task of breaking the septum apart from the sphenoid sinus wall, in order to provide an opening therethrough, should ideally be done very quickly and very gently, to avoid tearing blood vessels and tissue and to thereby minimize trauma experienced by the patient.

In the past, a surgical tool or instrument has generally not been available which could perform the delicate task of properly breaking the nasal septum from the sphenoid sinus wall, and which at the same time was operable within the narrow confines of the nasal passage. Frequently, instruments used to detach the septum have not allowed a force to be applied, within the narrow boundaries of the nasal cavity, which was sufficient to abruptly or instantaneously break the septum free. Rather, the septum detachment procedure, using the available tools of the prior art, could require a period of thirty minutes or more. The total time for surgery, as well as fatigue experienced by the surgeon, were thereby significantly increased. Moreover, use of such prior art tools tended to increase traumatization and injury of the septum.

SUMMARY OF THE INVENTION

The invention is generally directed to a surgical instrument or like apparatus for breaking or spreading the septum, as described above, which is located within the nasal cavity of a patient. The apparatus includes a shaft or other elongated support member having an axis, a selected end, and another end in opposing relationship with the selected end. A first elongated jaw member is fixably joined to the support member at the selected end, the first jaw member extending along the axis a first distance from a specifed point on the support member. A second elongated jaw member is also joined to the support member at the selected end, and is pivotable with respect thereto between closed and open jaw positions. When the second jaw member is in the closed position, it extends along the axis a second distance from the specified point, wherein the second distance is greater than the first distance by a specified amount. The apparatus further includes a set of teeth which is fixably mounted on an end of the second jaw member, and is disposed to engage the septum. A handle component is joined to the support member at the opposing end thereof, the handle component being movable between closed and open handle positions. A mechanical linkage extends between the handle component and the second jaw member for moving the second jaw member between the closed and open jaw positions, as the handle component is moved between the closed and open handle positions, respectively. The instrument of the invention enables substantial force to be applied to the septum, at the point at which the septum joins the sphenoid sinus wall, so that the septum can be instantaneously cracked or broken free therefrom.

In a preferred embodiment, the second jaw member has a length which is substantially less than the length of the support member, as measured between the selected and opposing ends thereof. When the second jaw member is in its closed position the first and second jaw members are in close abutting relationship, and the two jaws are insertable through a passage having a diameter which does not exceed on the order of one eighth of an inch. Preferably, the first jaw member and the support member are formed together as an integral structure. Preferably also, the second jaw member is disposed to move laterally with respect to the axis of the support member, as the second jaw member moves between the closed and open jaw positions. Usefully, a second handle component is fixably joined to the support member. Stops are provided on the handle components to limit relative movement thereof, and to thereby selectively limit movement of the second jaw member and the amount of force which can be applied thereto.

OBJECTS OF THE INVENTION

An object of the invention is to provide an improved microsurgical instrument for forming a passage through the nasal cavity, as well as through other septa located within a human patient.

Another object is to provide an instrument of the above type which minimizes tearing and trauma of tissue and blood vessels around the septum.

Another object is to provide an instrument of the above type which is operable within a very narrow and confined passage or body cavity.

Another object is to provide an instrument of the above type for selectively applying a substantial force to structure located within the narrow cavity.

Another object is to provide an instrument of the above type for quickly or instantaneously separating the nasal septum from the sphenoid sinus wall.

These and other objects and advantages of the invention will become more readily apparent from the ensuing specification, taken together with the accompanying drawings.

DETAILED DESCRIPTION OF THE PREFERRED EMBODIMENT

Figure 1:
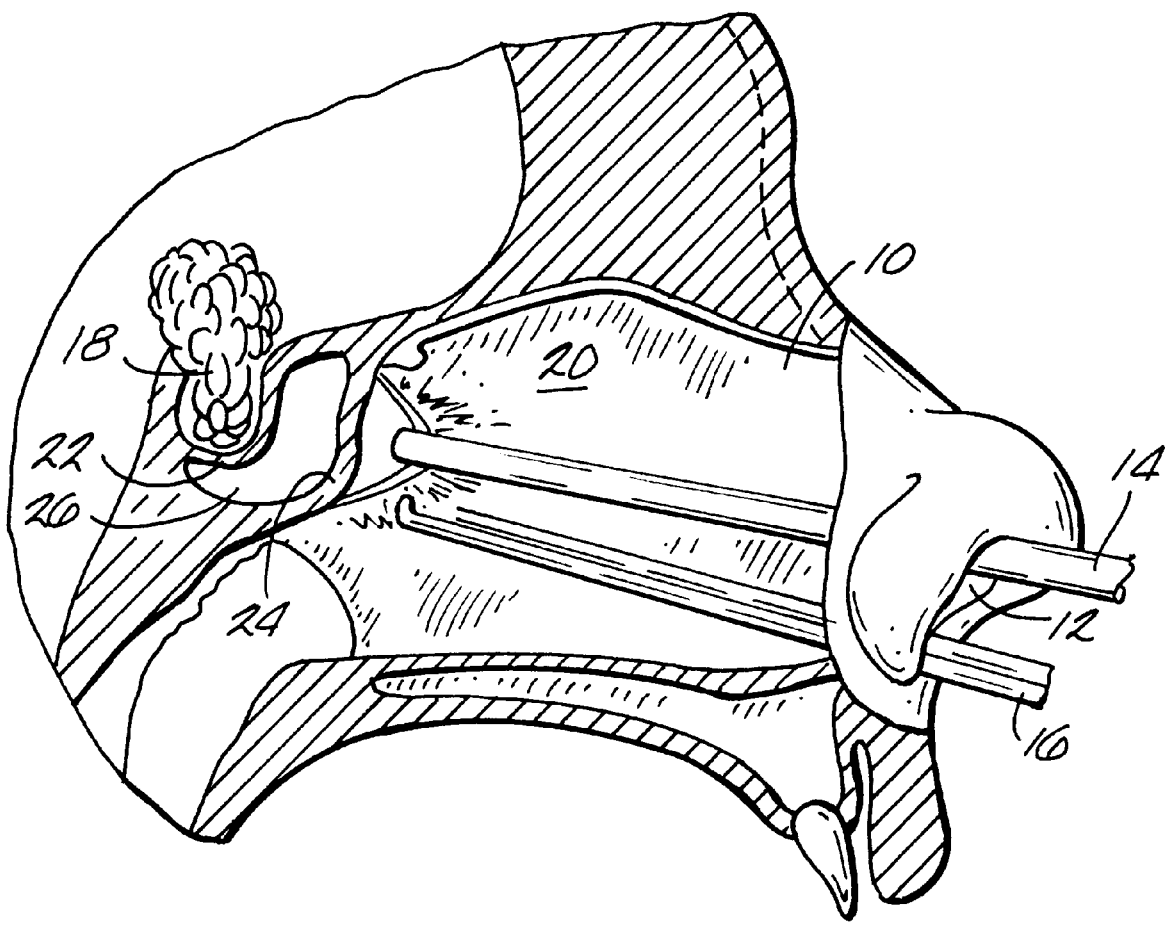
FIG. 1 is a perspective view having a section broken away to show the nasal cavity of a human patient, wherein an endoscope and a microsurgical instrument are inserted thereinto.

Referring to FIG. 1, there is shown a nasal cavity 10 of a patient, which may be accessed through the patient's nostril 12. An endoscope 14, as well as selected microsurgical instruments such as instrument 16, are inserted through nostril 12 to the rear of cavity 10, to surgically remove a pituitary tumor 18 located proximate thereto. The endoscope 14 enables the surgeon to view the region around the tumor, and different instruments are sequentially inserted into the cavity, in accordance with respective steps of the tumor removal procedure. The sella 22, which is a cup-shaped bone, is positioned between the rear of cavity 10 and the tumor 18. FIG. 1 further shows the nasal septum 20 of the patient, which comprises a wall extending along the nasal cavity 10. The septum 20 is vertically oriented as viewed in FIG. 1.

Figure 2:
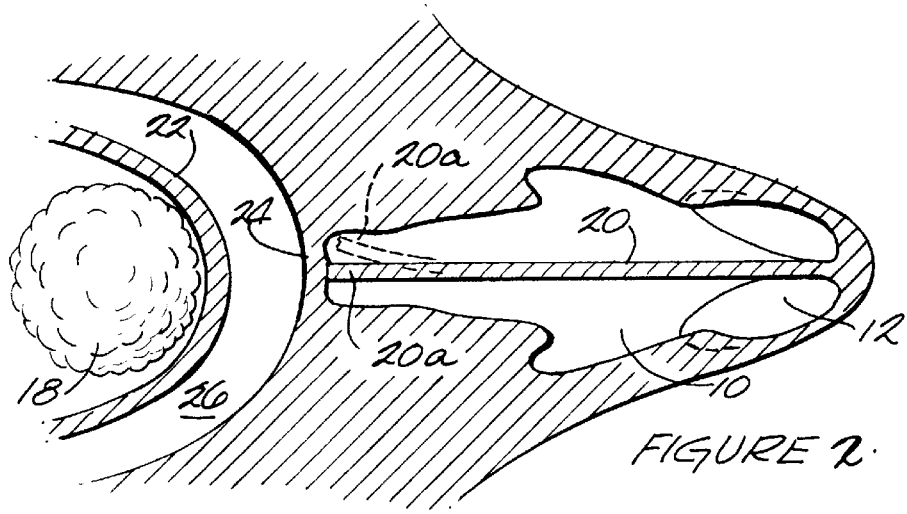
FIG. 2 is a horizontal sectional view taken through the nasal cavity shown in FIG. 1, and in particular shows the relationship between the septum, the sphenoid sinus, and the sphenoid sinus wall.

As best shown by FIG. 2, the rear edge 20a of the septum 20 is joined to the sphenoid sinus wall 24, a dome-shaped bone structure enclosing an air space known as the sphenoid sinus 26. Thus, in order for the endoscope 14 and instrument 16 to reach the sella and the tumor 18, a section of the sphenoid sinus wall 24 must be removed, to provide access to the sphenoid sinus 26. Before this can be done, however, the septum 20 must be detached from the sphenoid sinus wall 24. Also, the rear edge 20a of the septum should be urged sideward, as shown by the dashed line in FIG. 2, to increase the workspace available at the rear of the nasal cavity 10. As stated above, it is very desirable to perform the septum detachment procedure quickly, and to minimize the trauma experienced by the septum.

Figure 3:
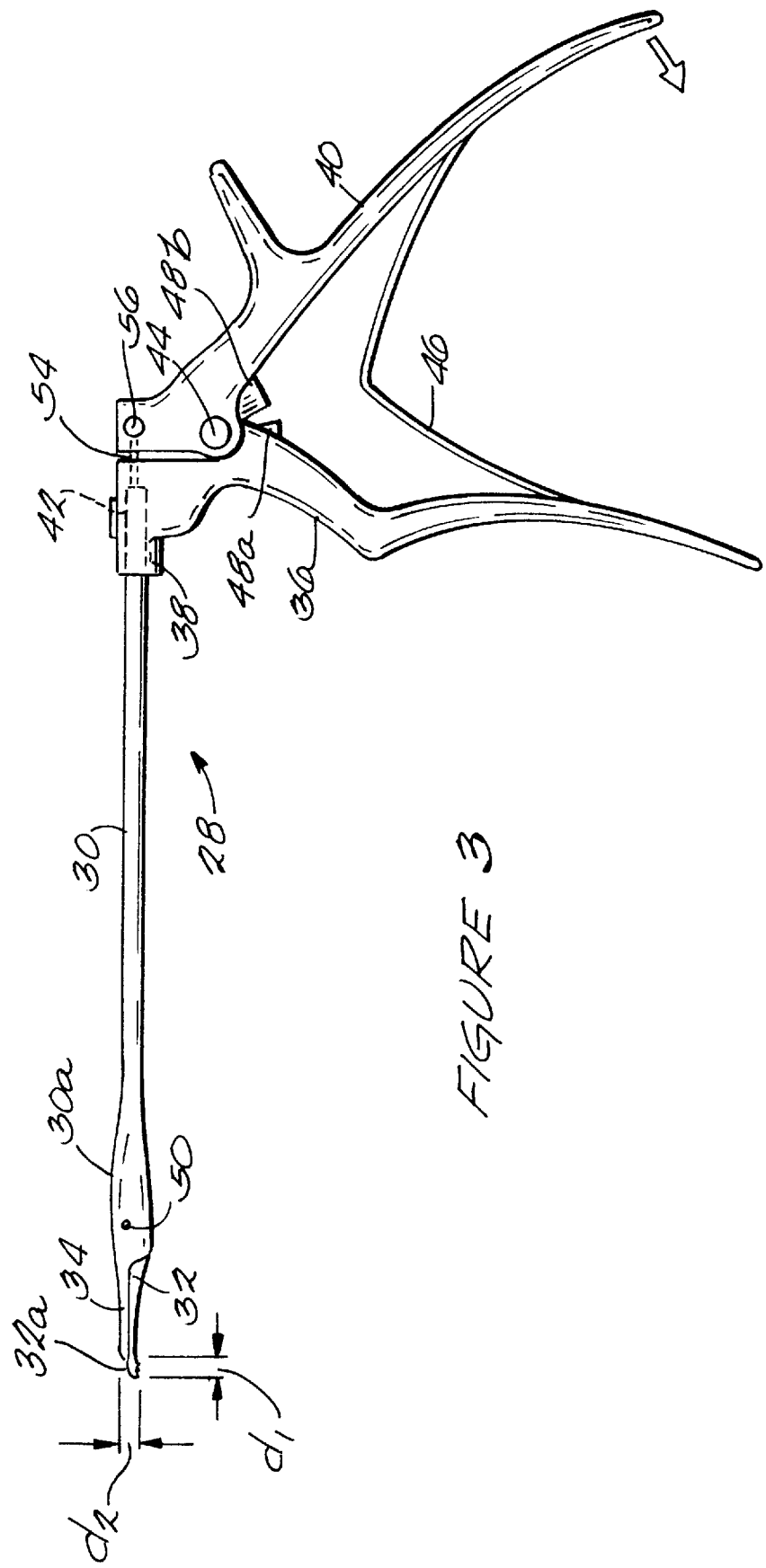
FIG. 3 is a perspective view showing an embodiment of the invention in its closed position.

Referring to FIG. 3, there is shown a nasal spreading or separating instrument 28, which includes a tubular shaft 30. A pivotable jaw member 32 and a fixed jaw member 34 are joined to the leftward end of shaft 30, as viewed in FIG. 3, and a fixed handle component 36 is joined to the rightward end thereof. Usefully, a sleeve member 38 is formed as an integral part of fixed handle component 36, and is provided with a socket sized to receive the end of shaft 30 in loose fitting relationship. Thus, shaft 30 may be rotated to any desired orientation with respect to fixed handle component 36. After a particular orientation has been selected, a set screw 42 is tightened, to hold shaft 30 in place with respect to handle component 36. Alternatively, a brazing operation may be used to hold shaft 30 in place with respect to handle component 36.

Figure 4:
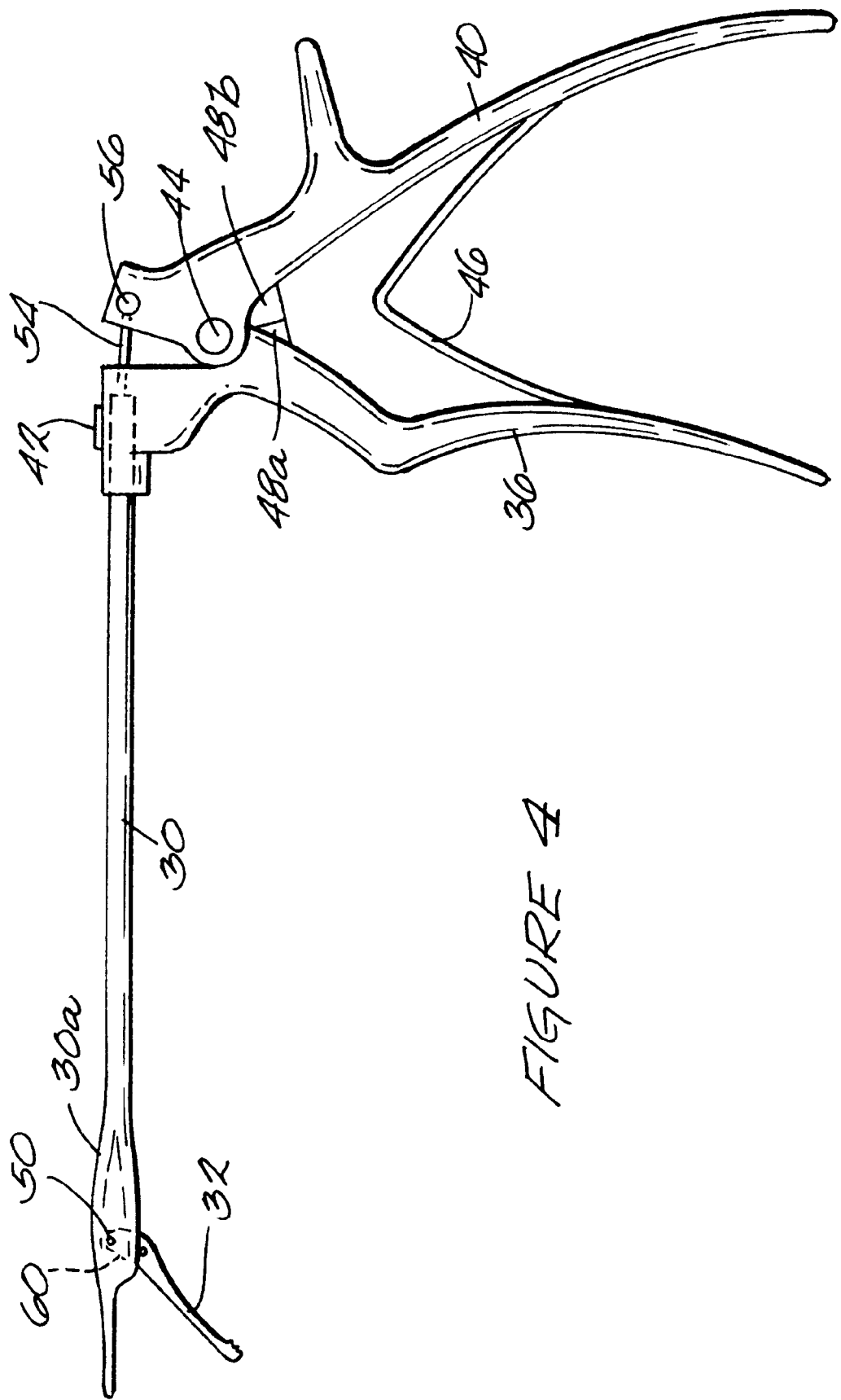
FIG. 4 is a perspective view showing the embodiment of FIG. 3 in its open position.

FIG. 3 further shows a movable handle component 40 which is pivotably joined to fixed handle component 36, such as by means of a pin 44. There is also shown a spring 46 positioned between handle components 36 and 40. The two handle components are respectively sized so that they can both be grasped at the same time by a user's hand, and receive a force therefrom which moves handle component 40 toward fixed handle component 36. Such movement, having the direction shown by the arrow in FIG. 3, can continue until stops 48a and 48b, mounted on handle components 36 and 40 respectively, are brought into abutting relationship as shown in FIG. 4. When the force applied to the handle components is released, spring 46 will urge handle component 40 back to the position thereof shown in FIG. 3.

Referring further to FIG. 3, there is shown pivotable jaw member 32 in a closed position, whereby it is in close abutting relationship with fixed jaw member 34. In the closed jaw position, both jaws 32 and 34 extend along the longitudinal axis of shaft 30, i.e., leftward as viewed in FIG. 3. It will be seen that the ends of jaws 32 and 34 extend to respective distances from a specified point on the shaft, such as the location of a pivot pin 50. For reasons descibed hereinafter, the end of pivotable jaw member 32 extends to a distance from pin 50 which is greater than the distance to which the end of fixed jaw member 34 extends, by an amount $d_1$.

Figure 5:
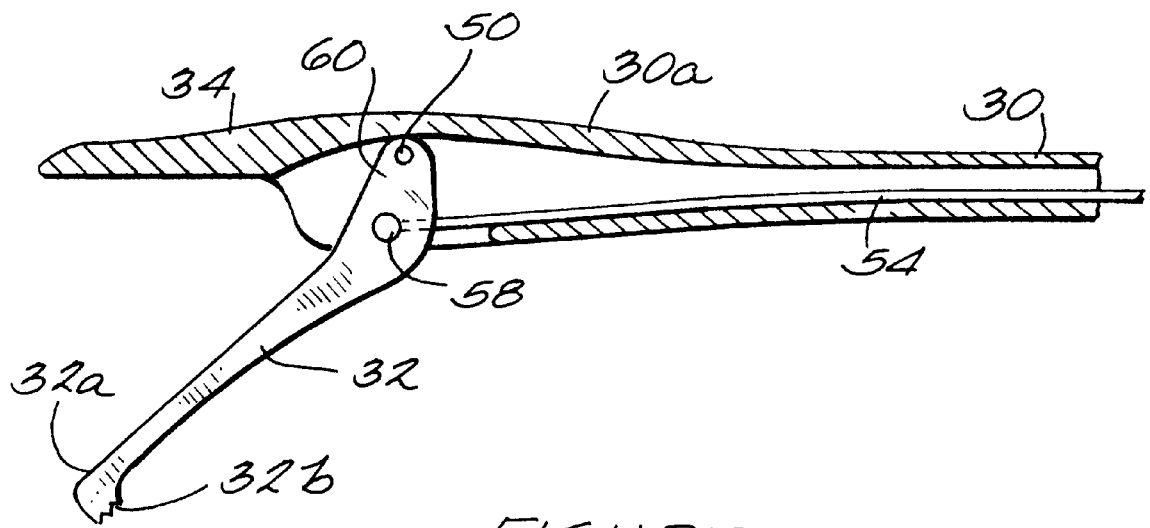
FIG. 5 shows a portion of the view shown in FIG. 4 in greater detail.

FIG. 3 further shows the end of pivotable jaw member 32 comprising an enlarged portion 32a. As best shown in FIG. 5, a number of teeth 32b are formed in enlarged jaw portion 32a, on the side of jaw member 32 which is opposite to the side thereof abutting jaw member 34, when jaw member 32 is in its closed position. FIGS. 3 and 5 also show teeth 32b pointing away from fixed jaw member 34 and in a direction which is generally orthogonal to the axis of shaft 30. However, even though the end of pivotable jaw member 32 is enlarged, when jaw member 32 is in its closed position the ends of jaw members 32 and 34 together are still small enough to fit through an opening having a diameter $d_2$ which is no greater than 0.125 inch.

Referring further to FIG. 3, there is shown the end of shaft 30 which is proximate to the jaw members comprising an enlarged shaft portion 30a. Preferably, the fixed jaw member 34 is formed as an integral structure with shaft 30.

As best shown by FIGS. 4 and 5, a rod 54 extends through shaft 30, one end of the rod being secured to movable handle component 40 by means of rounded end 56, and the other end being attached by means of a pin 58 to a cam 60, which is joined to pivotable jaw member 32. Preferably, cam 60 and jaw member 32 comprise an integral structure. Cam 60 is pivotably joined to enlarged portion 30a of shaft 30 by means of pivot pin 50, and resides within the enlarged shaft portion 30a when pivotable jaw member 32 is in its closed position. However, when handle component 40 is moved toward handle component 36, as shown in FIG. 4, rod 54 is pulled to the right, as viewed in FIG. 4. Cam 60 and jaw member 32 are thereby pivoted downward, as viewed in FIGS. 4 and 5, so that jaw member 32 is moved into an open jaw position. A slot is provided in enlarged shaft portion 30a, to allow such movement.

By providing the above arrangement for moving pivotable jaw member 32, it has been found that a user, simply by closing his hand to urge handle component 40 toward handle component 36, can operate jaw member 32 to apply a force of 15 pounds or greater to structure, such as septum 20, which is engaged thereby. At the same time, the stops 48a and 48b on the handle components provide a useful safety feature, to place a limit on the amount of force which can be applied to rod 54, and thereby to the jaw member 32 and the pivot pin 50. For example, the stops may be designed so that no force greater than 10 pounds can be applied to jaw member 32, regardless of the user's hand strength.

Figure 6:
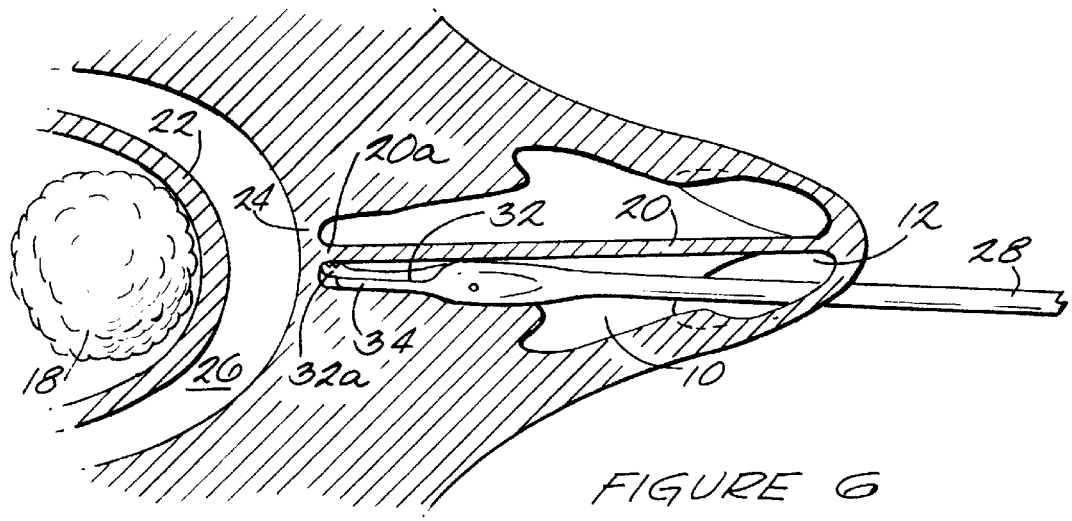
FIGS. 6 and 7 are sectional views respectively showing the embodiment of FIG. 3 inserted into a nasal cavity, and operated therein to detach and displace the nasal septum of a patient from the sphenoid sinus wall.

Referring to FIG. 6, there is shown instrument 28 inserted into nasal cavity 10 in its closed position, through nostril 12. More particularly, instrument 28 is inserted so that the end 32a of pivotable jaw member 32 reaches into the rearmost recess of cavity 10. This is achieved, in part, by providing pivotable jaw member 32 with the additional length $d_1$, referred to above, as compared with the length of fixed jaw member 34. Thus, the end 32a can extend into the farthest end of cavity 10, even when the cavity becomes very narrow at such position. Usefully, $d_1$, is on the order of 0.075 inches. FIG. 6 further shows instrument 28 oriented so that the teeth 32b of pivotable jaw member 32 engage the septum 20 at the location where it attaches to sphenoid sinus wall 24, that is, at the edge 20a thereof.

Figure 7:
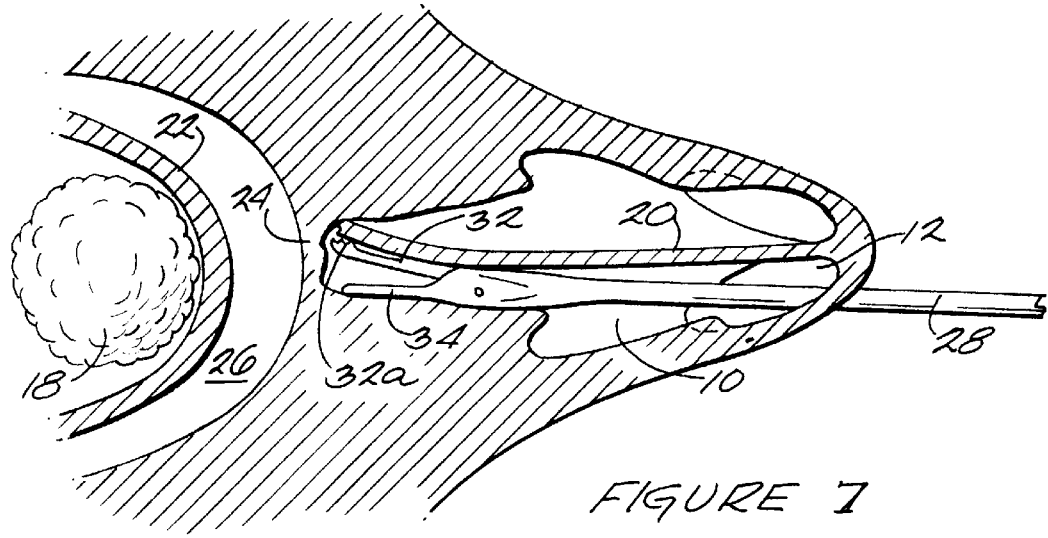

Referring to FIG. 7, there is shown instrument 28 operated as described above to move pivotable jaw member 32 into its open position. It is to be understood that because of the design of instrument 28, the leveraging action of jaw member 32, as it moves, applies substantial force to septum 20 along the edge 20a thereof. Such force causes the septum 20 to immediately be cracked or broken free from its attachment to the sphenoid sinus wall 24, and to be urged sideward with respect to nasal cavity 10. The breakage of the septum is comparatively clean, and is enhanced by providing the end 32a of jaw member 32 with teeth 32b, which bear against edge 20a of the septum.

Referring further to FIG. 7, there is shown fixed jaw member 34 bearing against the wall of cavity 10 which is in opposing relation with septum 20, to provide support for pivotable jaw member 32 as the jaw member 32 pushes against septum 20 to detach edge 20a.

Figure 8:
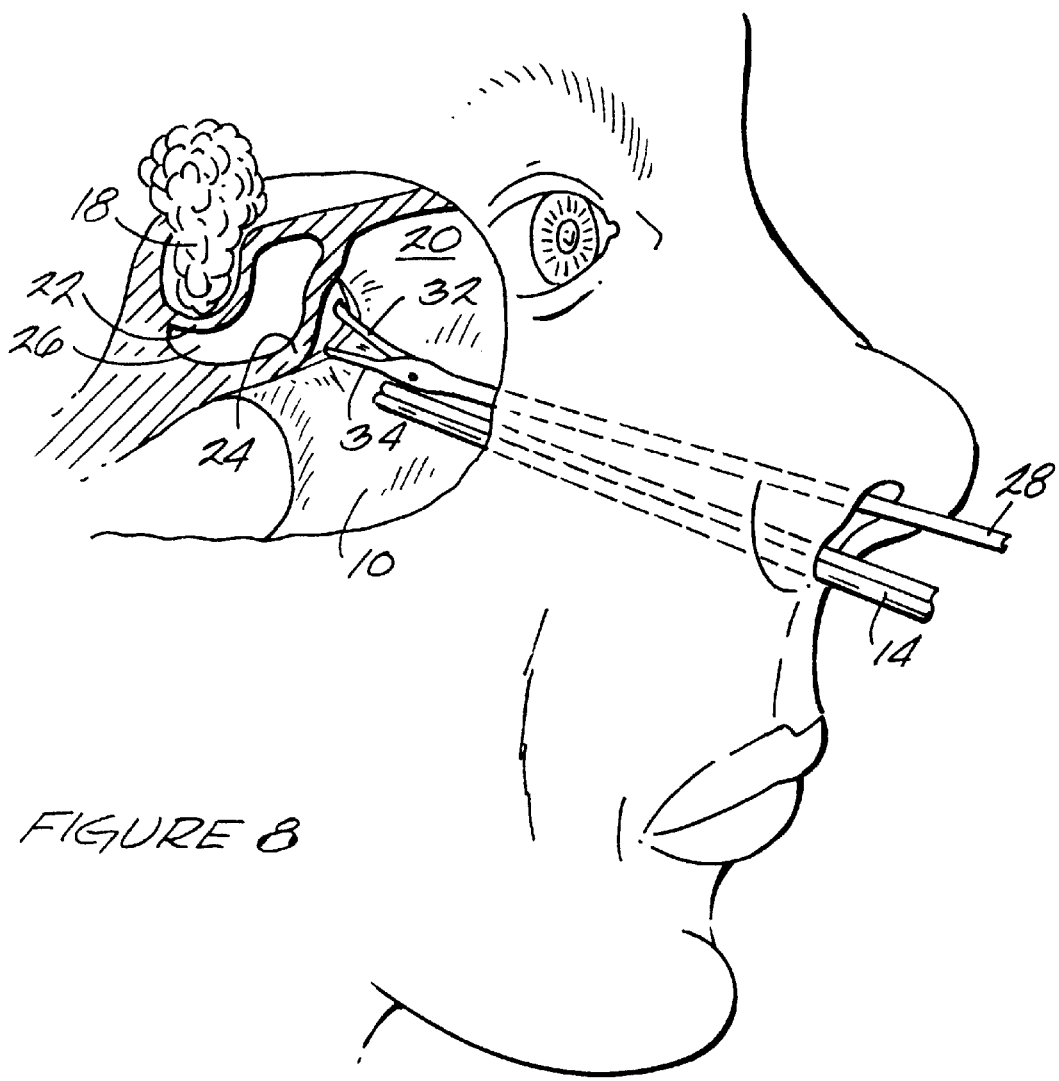
FIG. 8 is a perspective view showing the embodiment of FIG. 3 and an endoscope in operation.

FIG. 8 shows the instrument 28, together with an endoscope 14, operable in the nasal cavity of a patient to displace the nasal septum 20 as described above. It is to be understood that the length of pivotable jaw member 32 is on the order of 0.5 inch, whereas the length of shaft 30 is on the order of 5.5 inches. Such relationship between the length of the jaw members and the shaft enables the jaws to be effectively operated to form the opening within the very narrow confines of the nasal cavity.

Figure 9:
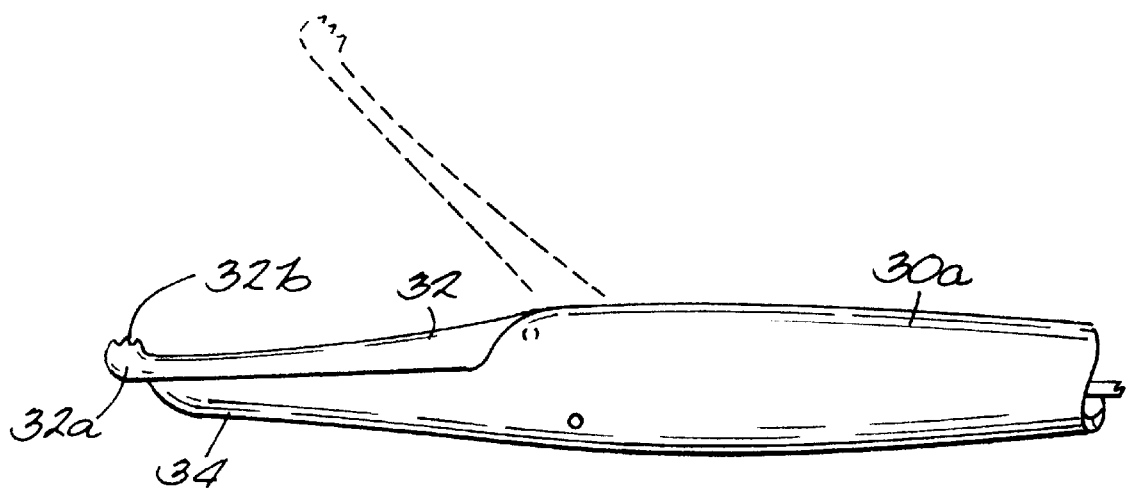
FIG. 9 is a perspective view showing a modification of the embodiment of FIG. 3.

Referring to FIG. 9, there is shown a portion of instrument 28 wherein shaft 30 and the jaw members have been rotated to an orientation with respect to handle components 36 and 40 such that jaw member 32 will move upwardly, rather than downwardly as shown in FIGS. 4 and 5, as it is urged to its open position. More generally, it will be understood that the plane through which jaw member 32 moves can be adjusted to virtually any angle, with respect to the plane of the handle components.

Obviously, other modifications and variations of the present invention are possible in light of the above teachings. It is therefore to be understood that within the scope of the disclosed concept, the invention may be practiced otherwise than as specifically described.

What is claimed is:

1. Surgical apparatus for spreading apart tissue located within a body cavity of a patient, said apparatus comprising:

an elongated support member having an axis, a first selected end, and a second end opposing said selected end;

a first elongated jaw member fixably joined to said support member at said selected end, said first jaw member extending along said axis to a first distance from a specified point on said support member;

a second elongated jaw member joined to said support member at said selected end, and pivotable with respect thereto between closed and open jaw positions, said second jaw member, when in said closed position, extending along said axis to a second distance from said specified point which is greater than said first distance by a specified amount;

a set of teeth disposed to engage said tissue fixably mounted on an end of said second jaw member;

a handle component joined to said support member at said opposing end, and movable with respect thereto between first and second handle positions; and a mechanical linkage extending between said handle component and said second jaw member for moving said second jaw member between said closed and open jaw positions as said handle component is moved between said first and second handle positions, respectively.

2. The apparatus of claim 1 wherein:

said second jaw member has a length which is substantially less than the length of said support member, as measured between said selected and opposing ends.

3. The apparatus of claim 2 wherein:

said support member has a length which is greater than five times the length of said second jaw member.

4. The apparatus of claim 2 wherein:

said first and second jaw members are in close abutting relationship when said second jaw member is in said closed jaw position.

5. The apparatus of claim 2 wherein:

said jaw members are sized for insertion into the nasal cavity of said patient when said second jaw member is in said closed jaw position.

6. The apparatus of claim 2 wherein:

said jaws are sized for insertion into a passage having a diameter which does not exceed on the order of 0.125 inches, when said second jaw member is in said closed jaw position.

7. The apparatus of claim 2 wherein:

said set of teeth are fixably joined to a side of said second jaw member which is in opposing relationship to the side thereof abutting said first jaw member when said second jaw member is in said closed jaw position.

8. The apparatus of claim 2 wherein:

said teeth are adapted to engage the nasal septum of said patient proximate to the position at which said septum is attached to the sphenoid sinus wall of said patient.

9. The apparatus of claim 8 wherein:

said second jaw member is disposed to apply a force to said septum which is laterally directed with respect to said axis.

10. The apparatus of claim 2 wherein:

said support member and said first jaw member comprise an integral structure.

11. The apparatus of claim 2 wherein:

said moveable handle component is disposed for movement with respect to a second handle component which is fixably joined to said support member; and stops are placed between said handle components to limit movement of said moveable handle component, and to thereby limit the force which can be applied to said second jaw member through said mechanical linkage.

12. Surgical apparatus for selectively displacing at least a portion of a septum located within a body cavity of a patient, said apparatus comprising:

an elongated support member having first and second ends in opposing relationship;

pivotable and fixed jaw members respectively joined to said support member proximate to said first end, said pivotable jaw member having a length which exceeds the length of said fixed jaw member by a specified amount;

a handle component joined to said support member proximate to said second end and movable between first and second handle positions;

means extending between said handle component and said pivotable jaw member for moving said pivotable jaw member between closed and open jaw positions as said handle component is moved between said first and second handle positions, respectively; and means mounted on said pivotable jaw member for engaging said septum, and for urging at least a portion of said septum from a first septum position to a second septum position as said pivotable jaw member moves from said closed jaw position to said open jaw position.

13. The apparatus of claim 12 wherein:

said pivotable jaw member is mounted for lateral movement with respect to the axis of said support member.

14. The apparatus of claim 13 wherein:

said moving means comprises means for applying a force to said septum through said pivotable jaw member which is in excess of 10 pounds.

15. The apparatus of claim 13 wherein:

said septum is attached to the sphenoid sinus wall of said patient, and said moving means comprises means for applying a force to said septum through said pivotable jaw member which is sufficient to detach said septum from said sphenoid sinus wall .

16. The apparatus of claim 12 wherein:

said septum engaging means comprises a set of teeth.

17. The apparatus of claim 12 wherein:

said specified amount comprises on the order of 0.075 inch.

* * * * *